US007332590B2

(12) United States Patent
Nacht et al.

(10) Patent No.: US 7,332,590 B2
(45) Date of Patent: Feb. 19, 2008

(54) MOLECULAR CHARACTERISTICS OF NON-SMALL CELL LUNG CANCER

(75) Inventors: Mariana Nacht, Belmont, MA (US); Tatiana Dracheva, Rockville, MD (US); David Sidransky, Baltimore, MD (US); Stephen Madden, Sudbury, MA (US); Jin Jen, Brookeville, MD (US)

(73) Assignees: The United States of America as Represented by the Department of Health and Human Services, Washington, DC (US); Genzyme Corporation, Cambridge, MA (US); The Johns Hopkins University of Medicine, Baltimore, MD (US)

( * ) Notice: Subject to any disclaimer, the term of this patent is extended or adjusted under 35 U.S.C. 154(b) by 312 days.

(21) Appl. No.: 10/486,844

(22) PCT Filed: Aug. 16, 2002

(86) PCT No.: PCT/US02/26027

§ 371 (c)(1),
(2), (4) Date: Sep. 9, 2004

(87) PCT Pub. No.: WO03/015613

PCT Pub. Date: Feb. 27, 2003

(65) Prior Publication Data

US 2005/0136403 A1 Jun. 23, 2005

Related U.S. Application Data

(60) Provisional application No. 60/312,400, filed on Aug. 16, 2001.

(51) Int. Cl.
*C07H 21/02* (2006.01)
*C12Q 1/68* (2006.01)
*C01D 15/08* (2006.01)

(52) U.S. Cl. .................. 536/23.1; 435/6; 435/91.2; 424/9.1

(58) Field of Classification Search .............. 536/23.1; 435/6, 91.2; 424/9.1
See application file for complete search history.

(56) References Cited

U.S. PATENT DOCUMENTS 5,763,155 A 6/1998 Boon-Falleur et al.
6,489,159 B1 12/2002 Chenchik et al.
2003/0065157 A1* 4/2003 Lasek .................. 536/23.1

FOREIGN PATENT DOCUMENTS

WO WO 99/50278 10/1999
WO WO 99/60160 11/1999

OTHER PUBLICATIONS

Zachara et al. Lung, 1997, vol. 175, p. 321-332.*
Anttila et al. Cancer Research, 1995, vol. 55, p. 3305-3309.*
Wang et al., "Identification of Genes Differentially Over-Expressed in Lung Squamous Cell Carcinoma Using Combination of CDNA Subtraction and Microarray Analysis", Oncogene, vol. 19, No. 12, Mar. 16, 2000, p. 1519-1528.
McDoniels-Silvers et al., "Identification of Differentially Expressed Genes in Human Lung Adenocarcinomas and Squamous Cell Carcinomas", Proceedings of the Annual Meeting of the American Association for Cancer Research, vol. 41, No. 680, Mar. 2000, p. 680.
Crawford et al., "Normal Brochialepithelial Cell Expression of Glutathione Transferase P1, Glutathione Transferase M3 and Glutathione Peroxidase is Low in Subjects with Bronchogenic Carcinoma", Cancer Research, American Association for Cancer Research, vol. 60, No. 6, Mar. 15, 2000, pp. 1609-1618.
Nacht, M. et al., "Molecular characteristics of non-small cell lung cancer", *PNAS*, (Dec. 18, 2001), pp. 15203-15208, vol. 98, No. 26.
Chang, J., "Augmented Expression of Peroxiredoxin I in Lung Cancer," *Biochemical and Biophysical Research Communications*, 2001, pp. 507-512, vol. 289(2).
Fujino, S., "The clinical implication of glutathione S-transferase-$\pi$expression in lung cancer: An immunohistochemical study," *Oncology Reports*, 1997, pp. 311-313, vol. 4(2).
Hu, R., "A small praline-rich protein, sprl: Specific marker for squamous lung carcinoma," *Lung Cancer*, 1998, pp. 25-30, vol. 20.
Lee, J., Induction of Thioredoxin by Oxidative Stress and Overexpression of Thioredoxin in Lung Cancer Tissue, *Tuberculosis and Respiratory Diseases*, 1999, pp. 327-337, vol. 46(3).
Shimomoto, H., "Expression of Tumor Necrosis Factor Receptors in Human Lung Cancer Cells and Normal Lung Tissues," *Am. J. Respir. Cell and Mol. Biol.*, 1995, pp. 271-278, vol. 13.

* cited by examiner

*Primary Examiner*—Kenneth R. Horlick
*Assistant Examiner*—Joyce Tung
(74) *Attorney, Agent, or Firm*—Banner & Witcoff, Ltd.

(57) ABSTRACT

We used hierarchical clustering to examine gene expression profiles generated by serial analysis of gene expression (SAGE) in a total of nine normal lung epithelial cells and non-small cell lung cancers (NSCLC). Separation of normal and tumor samples, as well as histopathological subtypes, was evident using the 3,921 most abundant transcript tags. This distinction remained when just 115 highly differentially expressed transcript tags were used. Furthermore, these 115 transcript tags clustered into groups that were suggestive of the unique biological and pathological features of the different tissues examined. Adenocarcinomas were characterized by high-level expression of small airway-associated or immunologically related proteins, while squamous cell carcinomas overexpressed genes involved in cellular detoxification or antioxidation. The messages of two p53-regulated genes, $p21^{WAF1/CIP1}$ and 14-3-3σ, were consistently underexpressed in the adenocarcinomas, suggesting that the p53 pathway itself might be compromised in this cancer type. Gene expression observed by SAGE were consistent with the results obtained by quantitative real-time PCR or cDNA array analyses using 43 additional lung tumor and normal samples. Thus, although derived from only a few tissue libraries, molecular signatures of non-small cell lung cancer derived from SAGE most likely represent an unbiased yet distinctive molecular signature for human lung cancer.

23 Claims, 3 Drawing Sheets

MOLECULAR CHARACTERISTICS OF NON-SMALL CELL LUNG CANCER

This application claims priority to provisional U.S. Application Ser. No. 60/312,400, filed Aug. 16, 2001.

FIELD OF THE INVENTION

The invention relates to the field of cancer. In particular it relates to the areas of diagnostics and lung cancer.

BACKGROUND OF THE INVENTION

Lung cancer is the leading cause of cancer death worldwide and NSCLC accounts for nearly 80% of the disease (1). Based on cell morphology, adenocarcinoma and squamous are the most common types of NSCLC (2). Although the clinical courses of these tumors are similar, adenocarcinomas are characterized by peripheral location in the lung and often have activating mutations in the K-ras oncogene (3, 4). In contrast, squamous cell carcinomas are usually centrally located and more frequently carry p53 gene mutations (5). Furthermore, the etiology of squamous cell carcinoma is closely associated with tobacco smoking while the cause of adenocarcinoma remains unclear (6, 7). Although many molecular changes associated with NSCLC have been reported (8, 9), the global gene expression pattern associated with these two most common types of lung cancer has not be described. Understanding gene expression patterns in these major tumor types will uncover novel markers for disease detection as well as potential targets for rational therapy of lung cancer.

Several technologies are currently being utilized for gene expression profiling in human cancer (10). SAGE (11) is an open system that rapidly identifies any expressed transcript in a tissue of interest, including transcripts that had not been identified. This highly quantitative method can accurately identify the degree of expression for each transcript. Comparing SAGE profiles between the tumor and the corresponding normal tissues can readily identify genes differentially expressed in the two populations. Using this method, novel transcripts and molecular pathways have been discovered (12-14). In contrast, cDNA arrays represent a closed system that analyze relative expression levels of previously known genes or transcripts (15, 16). Because many thousands of genes can be placed on a single membrane or slide for rapid screening, studies have recently demonstrated molecular profiles of several human cancers (17-20).

Hierarchical clustering is a systematic method widely used in cDNA array data analysis where the difference between the expression patterns of many genes is generally within a few fold (21). We reasoned that because SAGE is highly quantitative, hierarchical clustering might be used to organize gene expression data generated by SAGE from just a few tissue libraries. To test this, SAGE tags from two of each libraries derived from primary adenocarcinomas, primary squamous cell carcinomas, normal lung small airway epithelial cells (SAEC), or normal bronchial/tracheal epithelial (NHBE) cells, and a lung adenocarcinoma cell line were used. SAGE tags showing the highest abundance were subjected to clustering analysis. Although each library was derived from a different individual, normal and tumor samples clustered in two separate branches while tissues of different cell types clustered together. Furthermore, SAGE tags clustered into biologically meaningful groups revealing the important molecular characteristics of these two most common NSCLC subtypes.

BRIEF SUMMARY OF THE INVENTION

The present invention provides a method of identifying a lung cancer as squamous cell carcinoma. According to the method an amount of a gene product of a gene in a lung cancer sample is determined. The gene is selected from the group consisting of: glutathione peroxidase (GPX; NM_002083), glutathione S-transferase M3 (GSTM3; NM_000849), aldoketoreductase family 1, member B 10 (NM_020299), peroxiredoxin 1 (PRDX1; NM_002574), small proline-rich protein 3 (SPRR3; NM_005416), and TNF receptor superfamily member 18 (TNFRSF18; NM004195). The amount of the gene product in the lung cancer sample is compared to the amount determined in a lung tissue sample which is non-pathological. An increased amount of the gene product in the lung cancer sample relative to the lung tissue sample which is non-pathological identifies the lung cancer as a squamous cell carcinoma.

The present invention provides a method of identifying a lung cancer as adenocarcinoma. According to the method an amount of a gene product of a small proline-rich protein 3 (SPRR3; NM_005416) gene in a lung cancer sample is determined. The amount of the gene product in the lung cancer sample is compared to the amount determined in a lung tissue sample which is non-pathological. A decreased amount of the gene product in the lung cancer sample relative to the lung tissue sample which is non-pathological identifies the lung cancer as adenocarcinoma.

The invention thus provides the art with a molecular diagnostic to supplement or replace histological features and/or clinical behavior.

BRIEF DESCRIPTION OF THE DRAWINGS

FIG. 1A-FIG. 1C show clustering and multidimensional scaling of the SAGE libraries. Only genes with total tag-counts of at least 10 are included. (FIG. 1A) Cluster of all nine SAGE libraries. Genes are aligned horizontally, libraries are shown vertically. Red, green and black colors indicate genes expressed at high, low, or moderate levels, respectively, in the indicated library. (FIG. 1B) Dendrogram of clustered libraries. (FIG. 1C) Multidimensional scaling indicating the relatedness of the nine libraries.

FIG. 2A-FIG. 2C show clustering and multidimensional scaling of the 115 genes differentially expressed ($p<0.001$) in 9 SAGE libraries. (FIG. 2A) Cluster of the 115 genes (left panel) with 3 main clusters (right panels) consisting of genes overexpressed in squamous cell carcinoma (upper), overexpressed in adenocarcinoma (middle) and underexpressed in adenocarcinoma (lower panel), respectively. † Indicates that this tag corresponds to more than one gene of the same family. * Indicates that this tag corresponds to more than one distinct gene. (FIG. 2B) Dendrogram of 9 clustered libraries, using 115 differentially expressed genes. (FIG. 2C) Multidimensional scaling of the libraries, using 115 differentially expressed genes. Tubulin beta polypeptide tag (SEQ ID NO:1), ribosomal protein L37 tag (SEQ ID NO:2), gastrointestinal glutathione peroxidase 2 tag (SEQ ID NO:3), transferrin receptor tag (p90, CD71) (SEQ ID NO:4), brain glutathione S-transferase M3 tag (SEQ ID NO:5), carboxylesterase 1 tag (SEQ ID NO:6), aldo-keto reductase family 1 member B10 tag (SEQ ID NO:7), peroxiredoxin 1 tag (SEQ ID NO:8), interferon, alpha-inducible protein 27 tag (SEQ ID NO:9), major histocompatibility complex, class I, B tag (SEQ ID NO:10), surfactant, pulmonary-associated protein A2 tag (SEQ ID NO:11), major histocompatibility complex, class II tag (SEQ ID NO:12), immunoglobulin heavy constant mu tag (SEQ NO:13), pronapsin A tag (SEQ ID NO:14), surfactant, pulmonary-associated protein B tag (SEQ ID NO:15), CD74 antigen tag (SEQ ID NO:16), immunoglobulin lambda locus tag (SEQ ID NO:17), immunoglobulin heavy constant gamma 3 tag (SEQ ID NO:18), immunoglobulin alpha 2 tag (SEQ ID NO:19), VPS28 protein tag (SEQ ID NO:20), beta-2-microglobulin tag (SEQ ID NO:21), mucin 1 tag (SEQ ID NO:22), WAF1/CIP1/P21tag (SEQ ID NO:23), no match tag (SEQ ID NO:24), ribosomal protein L13a tag (SEQ ID NO:25), S100-type calcium binding protein A14 tag (SEQ ID NO:26), keratin 19 tag (SEQ ID NO:27), keratin 17 tag (SEQ ID NO:28), keratin 6A tag (SEQ ID NO:29), keratin 5 tag (SEQ ID NO:30), small proline-rich protein 1B tag (cornifin) (SEQ ID NO:31), keratin 14 tag (SEQ ID NO:32), 14-3-3 sigma tag (SEQ ID NO:33), S100 calcium-binding protein A2 tag (SEQ ID NO:34), keratin 16 tag (SEQ ID NO:35).

FIG. 3A-FIG. 3B show a comparison of genes underexpressed in adenocarcinoma using Affymetrix GeneChips™ and SAGE libraries.

DETAILED DESCRIPTION OF THE INVENTION

It is a discovery of the present inventors that certain molecular markers can be used to distinguish between the two most common forms of lung cancer: adenocarcinoma and squamous cell carcinoma. By assessing the expression levels of certain genes in a sample tumor tissue relative to normal, non-pathological lung tissue, one can make a determination of which of these types the cancer represents.

Expression of any gene which has been found to be up-regulated or down-regulated in one or more cancer types can be measured. According to one preferred embodiment, a lung tissue can be diagnosed, prognosed, or treatment determined by ascertaining an expression pattern of one or more cancer markers. Such markers include, but are not limited to glutathione peroxidase (GPX; NM_002083), glutathione S-transferase M3 (GSTM3; NM_000849), aldoketoreductase family 1, member B 10 (NM_020299), peroxiredoxin 1 (PRDX1; NM_002574), small proline-rich protein 3 (SPRR3; NM_005416), and TNF receptor superfamily member 18 (TNFRSF18; NM004195). The amount of the gene product determined in a suspected cancer tissue is compared to the amount of the same gene product in a lung tissue sample which is non-pathological. An increased or decreased amount of the gene product in the lung cancer sample relative to the lung tissue sample which is non-pathological identifies the lung cancer by type. Using such markers, one can distinguish between squamous cell carcinoma and adenocarcinoma of the lung, for example.

Either mRNA or protein can be measured as a means of determining up- or down-regulation of a gene. Any technique known in the art for measuring such gene products can be used. Quantitative techniques are preferred, however semi-quantitative or qualitative techniques can also be used. Suitable techniques for measuring gene products include, but are not limited to SAGE analysis, DNA microarray analysis, Northern blot, Western blot, immunocytochemical analysis, and ELISA.

Control samples which can be used according to the present invention include any non-pathological sample of lung tissue. These can be isolated from the same individual as the suspected lung sample or from a different individual, whether related or not. Suitable cell types include lung small airway epithelial cells as well as bronchial/tracheal epithelial cells.

EXAMPLES

Example 1

Tumors and Cell Lines

Primary lung tumor tissues used for SAGE were obtained from Johns Hopkins Hospital following surgery for lung resection due to cancer, and as previously described (9). Histologically, the two squamous tumors were moderately differentiated squamous cell carcinomas while the two adenocarcinomas consisted of a well differentiated and a poorly differentiated tumor with a shared common feature of lymphoplasmacytic infiltrations in the adjacent alveolar septa. SAEC and NHBE cells were purchased from Clonetics/BioWhittaker, Inc. (Walkersville, Md.) and propagated following the manufacturer's instruction. We chose these two primary cell cultures as normal controls because they represented pure populations of lung epithelial cells from the small and large airways, respectively. Tumor RNA samples were either purchased from BioChain Inc. (Hayward, Calif.) or obtained in the same manner as samples used for SAGE (9). A549 cells were obtained as a gift from Dr. James Herman (Johns Hopkins Oncology Center).

Example 2

SAGE Libraries and SAGE Analysis

Total RNA samples were isolated by RNazol B (Tel-Test Inc., Friendswood, Tex.) according to the manufacturer's recommendations. Poly (A)$^+$ RNA was extracted using the Oligotex mRNA Mini Kit (Qiagen Inc., Valencia, Calif.) and the Dynabeads mRNA DIRECT Kit (Dynal A.S., Oslo, Norway). SAGE libraries were generated and the tags sequenced as described (11) (22). SAGE 300 software (URL address: http file type, www host server, domain name sagenet.org, subdirectory sage_protocol, subdirectory htm, was used to identify tag sequences and to quantify the abundance of each tag. The gene identity and UniGene cluster assignment of each SAGE tag was obtained using the tag-to-gene 'reliable' map (updated Apr. 23, 2001) from URL address: http file type, www host server, domain name ncbi.nlm.nih.gov, directory pub, subdirectory SAGE, subsubdirectory map and the table of UniGene clusters (updated May 23, 2001), from URL address: http file type, www host server, domain namencbi.nlm.nih.gov, directory UniGene.

Example 3

Normalization and Hierarchical Clustering Analysis

The "Cluster 2.11" program (URL address: http file type, domain name rana.1b1.gov,) was used for normalization and clustering of the SAGE data. Briefly, the normalization included logarithmic transformation of the data, followed by 10 cycles of centering the data on the median by samples, then by genes, each time scaling the sum of the squares in each sample and each gene to 1. The non-centered Pearson correlation was used for distance calculations and the weighted-average linkage was used for clustering as described (21).

Example 4

Multidimensional Scaling of Normal Lung and Tumor Samples

A classical multidimensional scaling method was used to determine the relatedness of each library analyzed by SAGE (23). Each sample was used to generate a unique library. A table of normalized expression levels for each gene in every library was used as a dissimilarity matrix. Normalization was performed using the "Cluster 2.11" program, as described above. Multidimensional scaling allows for the calculation of coordinates of objects if the distances between objects are known. The distances between the samples were calculated as $1-C_{nm}$, where $C_{nm}$ was the correlation coefficient between libraries n and m. The distance matrix spans an N-dimensional space, where N is the number of libraries in the study. Principal Component Analysis (23) was used to best fit the libraries into a 3-dimensional realm for presentation purposes.

Example 5

Statistical Analysis

The p-chance analysis [available in the SAGE 300 software and described in (21) was used to select genes most differentially expressed between each tumor and its corresponding normal controls. P-chance uses the Monte-Carlo method (24) to calculate the relative probability of detecting an expression difference equal to, or greater than, the observed expression difference between two samples by chance alone. For each tumor type, one of the two tumor libraries was first compared with the two corresponding normal libraries to select genes with a p-chance value of <0.001. At this p-chance, the false positive rate for all selected genes was <0.015. We next selected only those genes with consistent expression patterns in both tumor libraries of the same cell type and combined them with genes selected from the other tumor type using the same method.

Example 6

Real-Time Quantitative PCR Analysis

Five genes identified by SAGE as highly expressed in either adenocarcinomas or squamous cell carcinoma were analyzed by Real-time reverse transcription (RT)-PCR using 14 RNA samples from lung tumors and controls (25). The Real-time RT-PCR probes and primers were designed using Primer Express software (PE Biosystems, Foster City, Calif.). Primer sequences and reaction conditions are described in the supplemental material. The relative expression of each gene was calculated as the ratio of the average gene expression levels for tumors of the same cell type compared to its corresponding normal.

Example 7

Gene Expression Analysis Using GeneChip™

GeneChip™ U95A probe arrays were obtained from Affymetrix Inc.(Santa Clara, Calif.). A total of 32 RNA samples were individually prepared, hybridized to the GeneChip™, and scanned by a Hewlett-Packard (HP) GeneArray™ scanner as recommended by the manufacturer. Six internal GeneChip™ standards, β-actin, 18S rRNA, 28S rRNA, glyceraldehyde-3-phosphate dehydrogenase, transferrin receptor, and the transcription factor ISGF-3, were used as controls to ensure the quality of all samples tested.

Example 8

SAGE of NSCLC

A total of nine independent SAGE libraries were generated from five different normal and tumor tissues. A total of 18,300 independent clones were sequenced to generate 374,643 tags that represented 66,501 distinct transcripts (Table 1). Of the 23,056 distinct tags that appeared more than once in all nine libraries combined, 18,595 tags had at least one match to a UniGene cluster, 4,907 tags had multiple matches, 4,319 tags had no match, and 142 tags matched to mitochondrial DNA or ribosomal RNA sequences. Accounting for 7% potential sequencing errors (21) in tags that appeared only once in all nine libraries, the total number of distinct transcript tags identified is about 59,000. Although this number exceeds the current estimate of 30,000 to 40,000 genes predicted in the human genome (26, 27), the discrepancy could be accounted for by alternatively spliced transcripts and polyadenylation usage sites, which can result in multiple SAGE tags for the same gene (28, 29). Alternatively, since our transcript analysis was done on a limited number of tissues, it is possible that the current gene estimates are low.

TABLE 1

SAGE in NSCLC and normal lung bronchial epithelial cells.

| Tissue Source | No. Clones | No. Tags |
| --- | --- | --- |
| Normal Human Bronchial Epithelial Cells-1 (NHBE-1) | 3759 | 58,273 |
| Normal Human Bronchial Epithelial Cells-2 (NHBE-2) | 4046 | 59,885 |
| Normal Small Airway Epithelial Cells-1 (SAEC-1) | 838 | 21,318 |
| Normal Small Airway Epithelial Cells-2 (SAEC-2) | 1299 | 26,956 |
| Squamous Cell Carcinoma-A | 2259 | 56,817 |
| Squamous Cell Carcinoma-B | 2186 | 51,901 |
| Adenocarcinoma-A | 799 | 21,714 |
| Adenocarcinoma-B | 928 | 24,018 |
| Adenocarcinoma cell line A549 | 2186 | 53,752 |
| Total Number | 18,300 | 374,634 |

Summary:
No. unique libraries = 9
No. unique tags = 66,502
No. of unique tags that appear >1 = 23,056
No. matched to unique UniGene cluster = 18,652

Example 9

Hierarchical Clustering of Tumor and Normal Lung Tissues Based on SAGE

Figure 1:
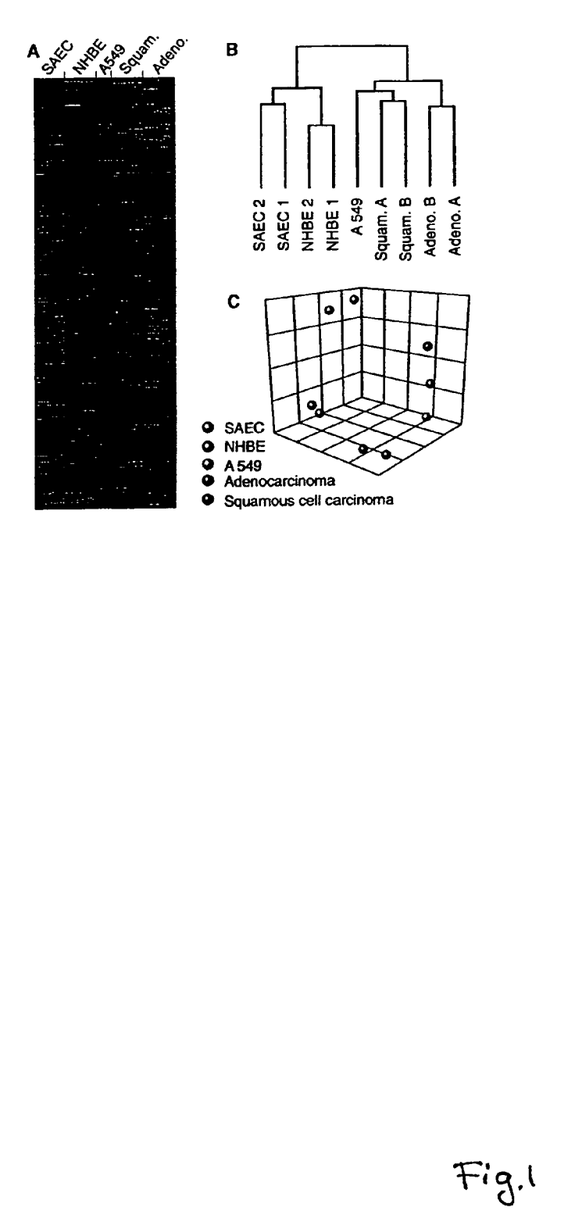

To identify genes that are differentially expressed between the tumors and the normal samples, as well as between the different tumor types, we examined the overall similarities of the libraries derived from each tissue using hierarchical clustering (22). Since expression differences for more commonly expressed genes are less likely to have been observed by chance, a collection of 3,921 SAGE tags appearing at least 10 times in all nine libraries was subjected to the clustering analysis. Although each sample was derived from a different individual and had a unique expression pattern (FIG. 1A), the normal tissues were more similar to each other and the tumor tissues were more alike as a group. Furthermore, the SAEC and NHBE samples each paired together under the normal branch, while the adenocarcinomas and the squamous cell tumors each clustered together under the tumor branch (FIG. 1B). The adenocarcinoma-derived A549 cell line branched with the NSCLC tumors and demonstrated its relatedness to the two adenocarcinomas in multi-dimensional scaling (23), which displays the spatial relationship of all nine samples with respect to one another (FIG. 1C).

Because gene expression levels were represented by a tag-count for each transcript detected in the SAGE libraries, we used the Monte-Carlo simulation (24) to quantify the significance of gene expression differences between the tumor libraries and the two corresponding normal epithelial cell controls. At a p<0.001, fifty-eight genes were selected when comparing the two adenocarcinomas to the two SAEC samples, and 71 genes were obtained by comparison of the squamous cell carcinomas to the NHBE cells. Because 14 genes were common to both of comparisons, we therefore identified 115 highly differentially expressed transcripts for both tumor types (Table 1, List of genes in *Supplemental Material*). As expected, when subjected to hierarchical clustering, these 115 genes again separated the nine libraries into the exact same branching patterns (FIG. 2A) as with the nearly 4,000 genes described above. Once again, the A549 cell line branched with the tumor tissues and was located closest to the two adenocarcinomas by multi-dimensional scaling (FIG. 2B).

Example 10

Biologically Distinct Clusters of Genes in Different NSCLC Subtypes

Figure 2:
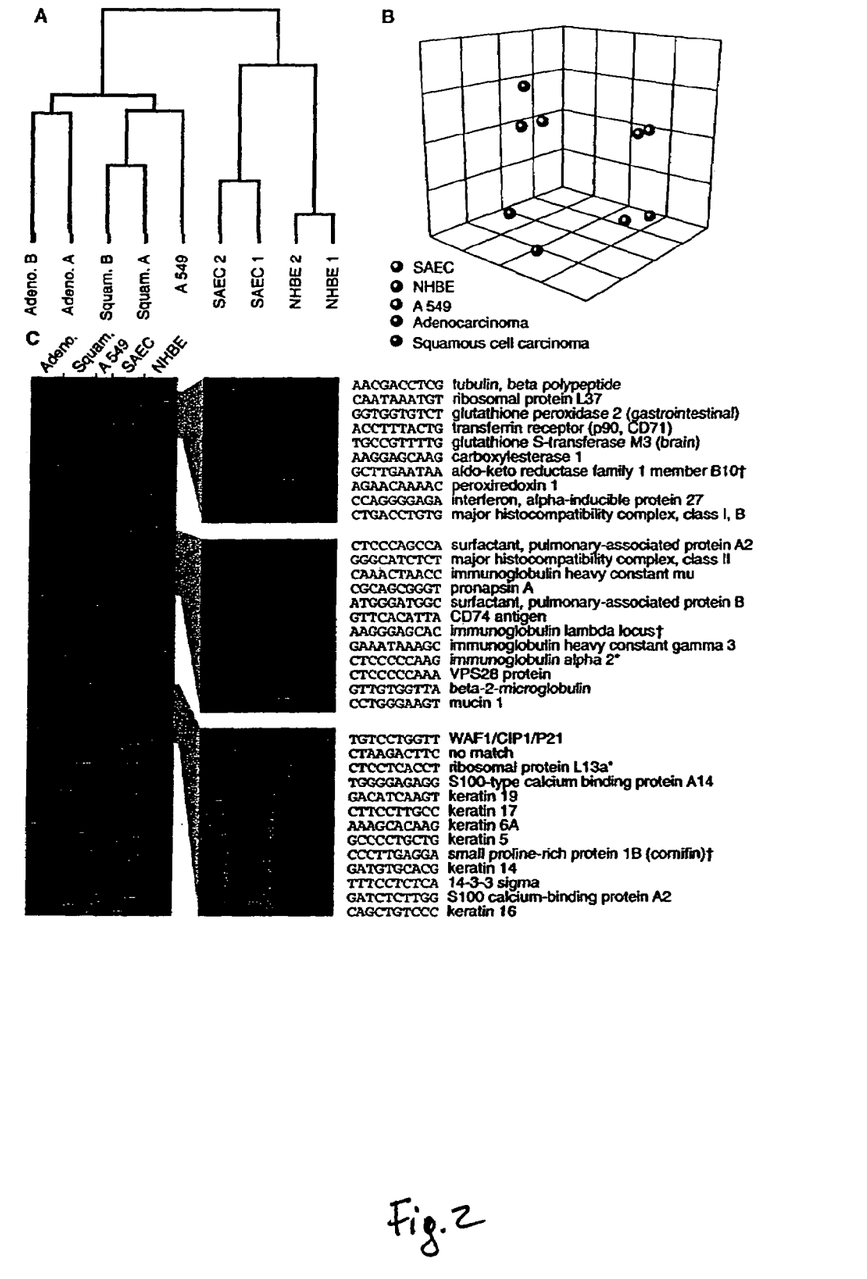

The clustering of the 115 statistically significant genes revealed at least three distinct gene clusters that were highly characteristic of the tumor tissues analyzed (FIG. 2C). Genes most highly expressed in squamous carcinomas of the lung (FIG. 2C, upper panel) were characterized by transcripts encoding proteins with detoxification and antioxidant properties. These genes include glutathione peroxidase 2 (GPX2), glutathione S-transferase M1 (GSTM1), carboxylesterase, aldo-keto reductase, and peroxiredoxin 1 (PRDX1). Their presence in squamous cell lung cancers most likely represented cellular response by the bronchial epithelium to environmental carcinogenic insults (30, 31). The clustering of these overexpressed genes highlight the notion that functional variation of these proteins in the population may contribute to lung cancer susceptibility in some patients. In addition, GSTM1 is a known susceptibility marker for lung and oral cavity cancer (32). It has also been associated with breast (33) and ovarian cancers (34). Interferon alpha-inducible protein 27 is also shown to be overexpressed in 50% of breast cancers (35).

In contrast, the cluster of genes overexpressed in lung adenocarcinoma (FIG. 2C, middle panel) mostly encoded small airway-associated proteins and immunologically related proteins. The presence of surfactants A2 and B, pronapsin A, and mucin 1 in the cluster reflects the origin of tumors derived from small airway epithelial cells, such as type 2 pneumocytes and Clara cells (36, 37). However, high expression of these genes also suggested that these proteins may participate in the tumorigenesis of lung adenocarcinomas. Indeed, mucin 1 is also overexpressed in breast cancers and tyrosine phosphorylation of the CT domain of MUC1 mucin leads to activation of a mitogen-activated protein kinase pathway through the Ras-MEK-ERK2 pathway (38, 39). Furthermore, the overexpression of immunoglobulin genes in adenocarcinomas examined may be explained by the extent of B-cell infiltration and the presence of antigen presenting cells (APC) in the adenocarcinomas used for SAGE analysis. However, clustering analyses of the SAGE tags revealed that different tumor types preferentially expressed a different set of cell surface markers. Squamous cell cancers appeared to overexpress MHC class I and CD71 proteins (FIG. 2C upper panel), while adenocarcinomas had a relatively high expression of MHC class II and CD 74 antigens. This gene expression differences in tumors indicated that immuno-based cancer therapy might be augmented based on the expression of different tumor surface markers.

No unexpected, many of the genes underexpressed in the primary adenocarcinomas and the A549 adenocarcinoma cell line (FIG. 2C, lower panel) were those that are associated with squamous differentiation. These proteins include S100 proteins, keratins, and the small proline-rich protein 1B (Cornifin). Interestingly, two p53-inducible genes, 14-3-3σ (Stratifin) (40) and $p21^{waf1/CIP1}$ (41, 42), clustered with this group of genes, showing significantly reduced expression in adenocarcinomas. Both $p21^{waf1/CIP1}$ and 14-3-3σ are highly induced in cells treated with ionizing radiation and other DNA damaging agents in a p53-dependent manner (43, 44). Induction of these genes by p53 leads to cell cycle arrest (45). The p53 gene is frequently mutated in squamous carcinomas of the lung, and it is thought that mutations in p53 may contribute to the inability of lung epithelial cells to repair carcinogen-induced damage (46). In contrast, p53 mutations are observed much less frequently in lung adenocarcinomas (5). The reduced expression of both $p21^{waf1/CIP1}$ and 14-3-3σ gene transcripts in adenocarcinomas suggests that inactivation of genes in the p53-pathway play an important role in this lung tumor type as well. However, reduced expression of an mRNA may not always correlate with a reduction of the gene product. Further studies correlating the molecular status of p53 with the expression of the encoded proteins are needed to assess the involvement of p53 and its downstream genes in the development of lung adenocarcinoma.

Example 11

Other Genes Differentially Expressed in NSCLC

It is important to note that the 115 highly differentially expressed genes we have identified only represented a set of genes whose differential expression could distinguish the molecular characteristics of each cell type as well as the neoplastic condition in the lung. Clearly, additional genes with biological significance to NSCLC could also be identified depending on the statistical method and the level of significance chosen. For example, when all tags that showed consistent expression within the libraries of the same cell type were compared to identify genes differentially expressed with a 99% confidence level, a larger number of candidate genes were identified. Specifically, 827 tags showed statistically significant differential expression between the squamous cell carcinomas and the NHBEs, with 71 tags showing at least 10-fold overexpression. A similar comparison of the two adenocarcinoma tumor libraries and the SAECs identified 298 tags showing differential expression, with 20 tags overexpressed at least 10-fold in the tumors. Jointly, 45 tags were differentially expressed in both comparisons and these genes were either a part of or further extended the observations revealed by the 115 genes. For example, small proline rich protein 3 (SPRR3) was elevated in the squamous tumors but was virtually absent in the adenocarcinomas. SPRR3 is a member of the small proline rich family of proteins which includes SPRR1 (Cornifin), a gene previously identified as a marker for squamous cell carcinoma (47) and is within the same cluster for genes underexpressed in adenocarcinomas (FIG. 2C lower panel). SPRR3 is a member of the proteins in the cornified cell envelope that help provide a protective barrier to the epidermal layer of cells (48). Reduced expression of this family of proteins in adenocarcinoma may contribute to the invasive properties of this cancer. Moreover, several members of the tumor necrosis factor (TNF) family of proteins and their receptors have demonstrated increased expression in various cancers including NSCLC (49). Our statistical analysis of the SAGE data revealed that expression of the TNF receptor superfamily member 18 gene was increased in squamous cell tumors in addition to the detocification and antioxidation genes. TNF promotes T-cell mediated apoptosis (50) and elevated expression of genes in this pathway may provide a mechanism for anti-proliferation of the tumor cells.

Example 12

Quantitative PCR and GeneChip™ cDNA Oligoarray Analyses of Additional NSCLC Tumors Because SAGE libraries were derived from only selected tumor tissues, it was essential to determine whether gene expression patterns derived from SAGE could be reproduced in larger panel lung tissues using independent assays. A total of 43 additional tumor and normal samples were examined using either quantitative real-time PCR or cDNA arrays methods. Five genes observed by SAGE as highly overexpressed in either squamous or adenocarcinomas of the lung (listed in FIG. 2C) were examined by Real-time RT-PCR using 10 different NSCLC tumors and four normal controls. As shown in Table 2, Real-time RT-PCR indicated that the two squamous-tumor specific genes had consistently high expression ratios in this tumor type compared to its expression in adenocarcinomas. Similarly, the three adenocarcinoma-specific genes had consistently higher expression in this tumor type and much less in squamous cell cancers compared to the normal.

TABLE 2

Real-time quantitative PCR analysis of SAGE-identified genes.

| | | | | No. of SAGE tags in library* | | | | | | | | Ave. RT-PCR[†] | |
|---|---|---|---|---|---|---|---|---|---|---|---|---|---|
| Spec. | Tag | Accession | Description | N1 | N2 | S1 | S2 | Sq A | Sq B | Ad A | Ad B | Sq/N | Ad/S |
| Sq | GGTGGTGTCT (SEQ ID NO:3) | X53463 | Glutathione peroxidase 2 (GPX2) | 4 | 2 | 0 | 1 | 58 | 41 | 0 | 0 | 11 | 2 |
| Sq | GCCCCCTTCC (SEQ ID NO:36) | AF241229 | TNF receptor superfamily member 18 | 0 | 1 | 0 | 0 | 11 | 8 | 0 | 0 | 38 | 5 |
| Ad | GAAATAAAGC (SEQ ID NO:18) | Y14737 | Ig heavy constant gamma 3 | 0 | 0 | 0 | 0 | 5 | 1 | 293 | 23 | 1 | 17 |
| Ad | GTTCACATTA (SEQ ID NO:16) | AI248864 | CD74 antigen | 0 | 1 | 0 | 1 | 9 | 2 | 86 | 21 | 31 | 93 |
| Ad | GGGCATCTCT (SEQ ID NO:12) | J00196 | Major histocompatibility complex, class II | 0 | 0 | 0 | 0 | 1 | 1 | 51 | 19 | 275 | 1800 |

Expression of the listed genes was examined in 14 samples, including five squamous cell tumors, four adenocarcinomas, one tumor with adenosquamous morphology, two NHBE cultures and two SAEC cultures.
*The actual number of tag occurrences in the indicated SAGE library is provided.
[†]The average expression of each gene was calculated for the four distinct cell types, and the ratio of differential expression is indicated.
Ad—Adenocarcinoma, Sq = squamous cell carcinoma, N = NHBE, S = SAEC, Spec. = Tumor specificity based on SAGE.

Figure 3A:
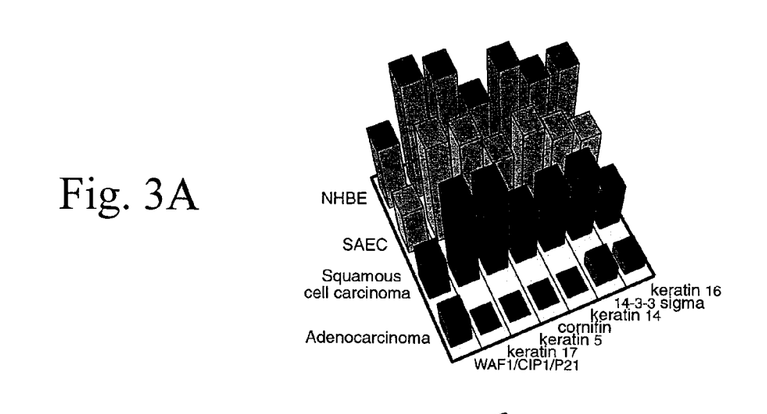
(FIG. 3A) Histogram of normalized SAGE data shows the average relative expression levels of 7 genes that were underexpressed in adenocarcinoma (shown in the lower right panel in FIG. 2C).
Figure 3B:
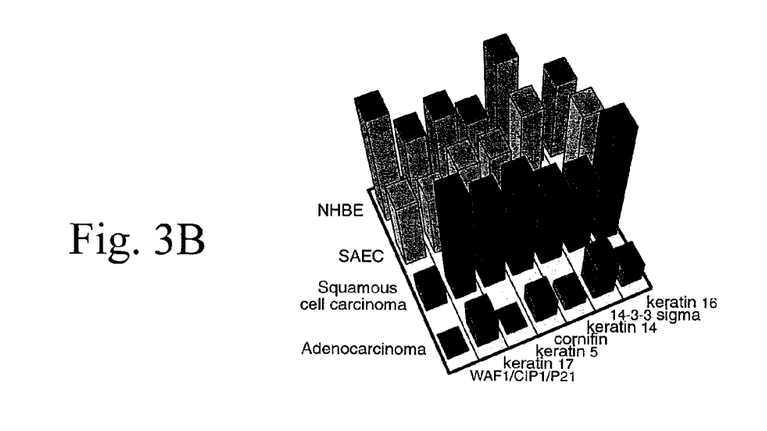
(FIG. 3B) Histogram of GeneChip™ data shows the normalized average relative expression levels of the same genes as in FIG. 3A. When a GeneChip™ expression value was less than 1, it was set to 1 before normalization. Normalization was done in the same manner as for clustering analysis.

In order to survey the overall reliability of the molecular clustering obtained from lung SAGE libraries, we used GeneChip™ cDNA oligoarray (15, 16) to survey 32 tumor and normal samples (including three samples used in Real-time PCR) for relative gene expression. Only 51 of 115 highly differentially expressed transcript tags were present in the 12,000 element GeneChip™ (U95A), and 20 of 35 genes from the three main clusters (shown in FIG. 2C) were comparable by both SAGE and the cDNA array. The gene expression levels for these 20 genes were averaged among all tumors of the same cell type and compared to that of the corresponding normal samples. Nineteen of 20 genes displayed an expression pattern similar to those obtained by SAGE. The expression patterns for the cluster of genes down-regulated in adenocarcinomas are shown (FIGS. 3A and 3B). These results indicate that hierarchical clustering of the SAGE libraries can reveal gene clusters with strong biological significance and support the notion that the highly quantitative and reproducible nature of SAGE can result in highly precise tissue classification and reliable gene clustering, using only a few tissue samples. Furthermore, because SAGE method is independent of the knowledge of the gene sequence or the probe hybridization condition, it allows for an unbiased identification and quantification of gene expression patterns in the tissues of interest. The use of SAGE can offer the opportunity to identify novel genes and molecular markers In summary, we have used SAGE and hierarchical clustering analysis to identify molecular profiles and clusters of genes specifically associated with two of the most common types of human lung cancer. Although biologically significant and highly reproducible, the gene expression profile described here may only represented the basic molecular features from which adenocarcinoma and squamous cell carcinoma of the lung can potentially be distinguished. Histological features and clinical behavior of the tumor may depend on less pronounced changes in expression levels for a variety of genes and pathways. Nevertheless, cumulating evidence suggests that gene expression patterns most likely determine the clinical behavior and therapeutic response of the cancer (19, 51). The list of highly differentially expressed genes that we described will likely provide new molecular targets for improved diagnosis, prognosis, and rational therapy. The analyses for the expression of these in a larger number of lung tumors with detailed clinical information and outcome will be help to accomplish this goal.

While the invention has been described with respect to specific examples including presently preferred modes of carrying out the invention, those skilled in the art will appreciate that there are numerous variations and permutations of the above described techniques that fall within the spirit and scope of the invention as set forth in the appended claims.

REFERENCES

1. American Cancer Society (2001) *Cancer Facts and Figures* 2001, Atlanta Ga.).
2. Travis, W. D., Linder, J. & Mackay, B. (1996) in *Lung Cancer Principles and Practice*, eds. Pass, H. I., Mitchell, J. B., Johnson, D. H. & Turrisi, A. T. (Lippincott-Raven, New York), pp. 361-395.
3. Gazdar, A. F. (1994) *Anticancer Res* 14, 261-7.
4. Graziano, S. L., Gamble, G. P., Newman, N. B., Abbott, L. Z., Rooney, M., Mookherjee, S., Lamb, M. L., Kohman, L. J. & Poiesz, B. J. (1999) *J Clin Oncol* 17, 668-75.
5. Niklinska, W., Chyczewski, L., Laudanski, J., Sawicki, B. & Niklinski, J. (2001) *Folia Histochem Cytobiol* 39, 147-8.
6. Bennett, W. P., Hussain, S. P., Vahakangas, K. H., Khan, M. A., Shields, P. G. & Harris, C. C. (1999) *J Pathol* 187, 8-18.
7. Hainaut, P. & Pfeifer, G. P. (2001) *Carcinogenesis* 22, 367-74.
8. Forgacs, E., Zochbauer-Muller, S., Olah, E. & Minna, J. D. (2001) *Pathol Oncol Res* 7, 6-13.
9. Hibi, K, Liu, Q., Beaudry, G. A., Madden, S. L., Westra, W. H., Wehage, S. L., Yang, S. C., Heitmiller, R. F., Bertelsen, A. H., Sidransky, D., et al. (1998) *Cancer Res* 58, 5690-4.
10. Gray, J. W. & Collins, C. (2000) *Carcinogenesis* 21, 443-52.
11. Velculescu, V. E., Zhang, L., Vogelstein, B. & Kinzler, K. W. (1995) *Science* 270, 484-7.
12. Polyak, K., Xia, Y., Zweier, J. L., Kinzler, K. W. & Vogelstein, B. (1997) *Nature* 389, 300-5.
13. He, T. C., Sparks, A. B., Rago, C., Hermeking, H., Zawel, L., da Costa, L. T., Morin, P. J., Vogelstein, B. & Kinzler, K. W. (1998) *Science* 281, 1509-12.
14. Hermeking, H., Rago, C., Schuhmacher, M., Li, Q., Barrett, J. F., Obaya, A. J., O'Connell, B. C., Mateyak, M. K., Tam, W., Kohlhuber, F., et al. (2000) *Proc Natl Acad Sci USA* 97, 2229-34.
15. DeRisi, J., Penland, L., Brown, P. O., Bittner, M. L., Meltzer, P. S., Ray, M., Chen, Y., Su, Y. A. & Trent, J. M. (1996) *Nat Genet* 14, 457-60.
16. Jordan, B. R. (1998) *J Biochem* (Tokyo) 124, 251-8.
17. Alizadeh, A. A., Eisen, M. B., Davis, R. E., Ma, C., Lossos, I. S., Rosenwald, A., Boldrick, J. C., Sabet, H., Tran, T., Yu, X., et al. (2000) *Nature* 403, 503-11.
18. Perou, C. M., Sorlie, T., Eisen, M. B., van de Rijn, M., Jeffrey, S. S., Rees, C. A., Pollack, J. R., Ross, D. T., Johnsen, H., Akslen, L. A., et al. (2000) *Nature* 406, 747-52.
19. Hedenfalk, I., Duggan, D., Chen, Y., Radmacher, M., Bittner, M., Simon, R., Meltzer, P., Gusterson, B., Esteller, M., Kallioniemi, O. P., et al. (2001) *N Engl J Med* 344, 539-48.
20. Notterman, D. A., Alon, U., Sierk, A. J. & Levine, A. J. (2001) *Cancer Res* 61, 3124-30.
21. Eisen, M. B., Spellman, P. T., Brown, P. O. & Botstein, D. (1998) *Proc Natl Acad Sci USA* 95, 14863-8.
22. Zhang, L., Zhou, W., Velculescu, V. E., Kern, S. E., Hruban, R. H., Hamilton, S. R., Vogelstein, B. & Kinzler, K. W. (1997) *Science* 276, 1268-72.
23. Cox, T. F. & Cox, M. A. (2001) *Multidimensional Scaling* (Chapman and Hall/CRC, New York).
24. Hammersley, J. M. & Handscomb, D. C. (1964) *Monte Carlo Methods* (Wiley, New York).
25. Higuchi, R., Fockler, C., Dollinger, G. & Watson, R. (1993) *Biotechnology* 11, 1026-1030.
26. Lander, E. S., Linton, L. M., Birren, B., Nusbaum, C., Zody, M. C., Baldwin, J., Devon, K., Dewar, K., Doyle, M., FitzHugh, W., et al. (2001) *Nature* 409, 860-921.
27. Venter, J. C., Adams, M. D., Myers, E. W., Li, P. W., Mural, R. J., Sutton, G. G., Smith, H. O., Yandell, M., Evans, C. A., Holt, R. A., et al. (2001) *Science* 291, 1304-1351.
28. Mironov, A. A., Fickett, J. W. & Gelfand, M. S. (1999) *Genome Res* 9, 1288-93.
29. Brett, D., Hanke, J., Lehmann, G., Haase, S., Delbruck, S., Krueger, S., Reich, J. & Borka, P. (2000) *FEBS Lett* 474, 83-6.
30. Auerbach, O. (1980) in *Pulmonary Diseases and Disorders*, ed. Fishman, A. P. (McGraw-Hill, New York), pp. 1388-1396.
31. Sekido, Y., Fong, K. M. & Minna, J. D. (1998) *Biochim Biophys Acta* 1378, F21-59.
32. Nair, U. & Bartsch, H. (2001) *IARC Sci Publ* 154, 271-90.
33. Mitrunen, K., Jourenkova, N., Kataja, V., Eskelinen, M., Kosma, V. M., Benhamou, S., Vainio, H., Uusitupa, M. & Hirvonen, A. (2001) *Cancer Epidemiol Biomarkers Prev* 10, 229-36.
34. Howells, R. E., Holland, T., Dhar, K. K., Redman, C. W., Hand, P., Hoban, P. R., Jones, P. W., Fryer, A. A. & Strange, R. C. (2001) *Int J Gynecol Cancer* 11, 107-112.
35. Rasmussen, U. B., Wolf, C., Mattei, M. G., Chenard, M. P., Bellocq, J. P., Chambon, P., Rio, M. C. & Basset, P. (1993) *Cancer Res* 53, 4096-101.

36. Colby, T. V., Koss, M. N. & Travis, W. D. (1995), eds. Rosai, J. & Sobin, L. H. (Armed Forces Institute of Pathology, Washington, D.C.), pp. 10.
37. Chuman, Y., Bergman, A., Ueno, T., Saito, S., Sakaguchi, K., Alaiya, A. A., Franzen, B., Bergman, T., Arnott, D., Auer, G., et al. (1999) *FEBS Lett* 462, 129-34.
38. Taylor-Papadimitriou, J., Burchell, J., Miles, D. W. & Dalziel, M. (1999) *Biochim Biophys Acta* 1455, 301-13.
39. Meerzaman, D., Shapiro, P. S. & Kim, K. C. (2001) *Am J Physiol Lung Cell Mol Physiol* 281, L86-91.
40. Hermeking, H., Lengauer, C., Polyak, K., He, T. C., Zhang, L., Thiagalingam, S., Kinzler, K. W. & Vogelstein, B. (1997) *Mol Cell* 1, 3-11.
41. el-Deiry, W. S., Harper, J. W., O'Connor, P. M., Velculescu, V. E., Canman, C. E., Jackman, J., Pietenpol, J. A., Burrell, M., Hill, D. E., Wang, Y., et al. (1994) *Cancer Res* 54, 1169-74.
42. Harper, J. W., Adami, G. R., Wei, N., Keyomarsi, K. & Elledge, S. J. (1993) *Cell* 75, 805-16.
43. Waldman, T., Lengauer, C., Kinzler, K. W. & Vogelstein, B. (1996) *Nature* 381, 713-6.
44. Chan, T. A., Hermeking, H., Lengauer, C., Kinzler, K. W. & Vogelstein, B. (1999) *Nature* 401, 616-20.
45. Taylor, W. R. & Stark, G. R. (2001) *Oncogene* 20, 1803-15.
46. Therrien, J. P., Drouin, R., Baril, C. & Drobetsky, E. A. (1999) *Proc Natl Acad Sci USA* 96, 15038-43.
47. Hu, R., Wu, R., Deng, J. & Lau, D. (1998) *Lung Cancer* 20, 25-30.
48. De Heller-Milev, M., Huber, M., Panizzon, R. & Hohl, D. (2000) *Br J Dermatol* 143, 733-40.
49. Tran, T. A., Kallakury, B. V., Ambros, R. A. & Ross, J. S. (1998) *Cancer* 83, 276-82.
50. Holtzman, M. J., Green, J. M., Jayaraman, S. & Arch, R. H. (2000) *Apoptosis* 5, 459-71.
51. Scherf, U., Ross, D. T., Waltham, M., Smith, L. H., Lee, J. K., Tanabe, L., Kohn, K. W., Reinhold, W. C., Myers, T. G., Andrews, D. T., et al. (2000) *Nat Genet* 24, 236-44.

---

We claim:

1. A method of associating a lung cancer with squamous cell carcinoma comprising:

determining an amount of a gene product of a gene in a lung cancer sample, said gene selected from the group consisting of: aldoketoreductase family 1, member B 10 (NM_020299), peroxiredoxin 1 (PRDX1; NM_002574), and TNF receptor superfamily member 18 (TNFRSF18; NM004195);

comparing the amount of the gene product to the amount determined in a lung tissue sample which is non-pathological, wherein an increased amount of the gene product in the lung cancer sample relative to the lung tissue sample which is non-pathological associates the lung cancer with a squamous cell carcinoma.

2. The method of claim 1 further comprising the step of using the determined comparative gene product information to formulate a diagnosis.

3. The method of claim 1 further comprising the step of using the determined comparative gene product information to formulate a prognosis.

4. The method of claim 1 further comprising the step of using the determined comparative gene product information to formulate a treatment plan.

5. The method of claim 1 wherein the gene product of aldoketoreductase is determined.

6. The method of claim 1 wherein the gene product of PRDX1 is determined.

7. The method of claim 1 wherein the gene product of TNF receptor 18 is determined.

8. The method of claim 1 wherein the gene product is mRNA.

9. The method of claim 1 wherein the gene product is protein.

10. The method of claim 1 wherein the lung tissue sample which is non-pathological comprises normal lung small airway epithelial cells.

11. The method of claim 1 wherein the lung tissue sample which is non-pathological comprises normal bronchial/tracheal epithelial cells.

12. The method of claim 1 wherein the amount of the gene product is determined using a microarray.

13. The method of claim 12 wherein cRNA is hybridized to probes on the microarray to determine the amount of the gene product.

14. A method of associating a lung cancer with adenocarcinoma, comprising:

determining an amount of a gene product of a small proline-rich protein 3 (SPRR3; $NM_{13}$ 005416) gene in a lung cancer sample;

comparing the amount of the gene product to the amount determined in a lung tissue sample which is non-pathological. wherein a decreased amount of the gene product in the lung cancer sample relative to the lung tissue sample which is non-pathological associates the lung cancer with adenocarcinoma.

15. The method of claim 14 further comprising the step of using the determined comparative gene product information to formulate a diagnosis.

16. The method of claim 14 further comprising the step of using the determined comparative gene product information to formulate a prognosis.

17. The method of claim 14 further comprising the step of using the determined comparative gene product information to formulate a treatment plan.

18. The method of claim 14 wherein the gene product is mRNA.

19. The method of claim 14 wherein the gene product is protein.

20. The method of claim 14 wherein the lung tissue sample which is non-pathological comprises normal lung small airway epithelial cells.

21. The method of claim 14 wherein the lung tissue sample which is non-pathological comprises normal bronchial/tracheal epithelial cells.

22. The method of claim 14 wherein the amount of the gene product is determined using a microarray.

23. The method of claim 22 wherein cRNA is hybridized to probes on the microarray to determine the amount of the gene product.

* * * * *

SEQUENCE LISTING

<160> NUMBER OF SEQ ID NOS: 36

<210> SEQ ID NO 1
<211> LENGTH: 10
<212> TYPE: DNA
<213> ORGANISM: Homo sapiens

<400> SEQUENCE: 1
aacgacctcg                                                              10

<210> SEQ ID NO 2
<211> LENGTH: 10
<212> TYPE: DNA
<213> ORGANISM: Homo sapiens

<400> SEQUENCE: 2
caataaatgt                                                              10

<210> SEQ ID NO 3
<211> LENGTH: 10
<212> TYPE: DNA
<213> ORGANISM: Homo sapiens

<400> SEQUENCE: 3
ggtggtgtct                                                              10

<210> SEQ ID NO 4
<211> LENGTH: 10
<212> TYPE: DNA
<213> ORGANISM: Homo sapiens

<400> SEQUENCE: 4
acctttactg                                                              10

<210> SEQ ID NO 5
<211> LENGTH: 10
<212> TYPE: DNA
<213> ORGANISM: Homo sapiens

<400> SEQUENCE: 5
tgccgttttg                                                              10

```
<210> SEQ ID NO 6
<211> LENGTH: 10
<212> TYPE: DNA
<213> ORGANISM: Homo sapiens

<400> SEQUENCE: 6
aaggagcaag                                                          10

<210> SEQ ID NO 7
<211> LENGTH: 10
<212> TYPE: DNA
<213> ORGANISM: Homo sapiens

<400> SEQUENCE: 7
gcttgaataa                                                          10

<210> SEQ ID NO 8
<211> LENGTH: 10
<212> TYPE: DNA
<213> ORGANISM: Homo sapiens

<400> SEQUENCE: 8
agaacaaaac                                                          10

<210> SEQ ID NO 9
<211> LENGTH: 10
<212> TYPE: DNA
<213> ORGANISM: Homo sapiens

<400> SEQUENCE: 9
ccaggggaga                                                          10

<210> SEQ ID NO 10
<211> LENGTH: 10
<212> TYPE: DNA
<213> ORGANISM: Homo sapiens

<400> SEQUENCE: 10
ctgacctgtg                                                          10

<210> SEQ ID NO 11
<211> LENGTH: 10
<212> TYPE: DNA
<213> ORGANISM: Homo sapiens

<400> SEQUENCE: 11
ctcccagcca                                                          10

<210> SEQ ID NO 12
<211> LENGTH: 10
<212> TYPE: DNA
<213> ORGANISM: Homo sapiens

<400> SEQUENCE: 12
gggcatctct                                                          10

<210> SEQ ID NO 13
<211> LENGTH: 10
<212> TYPE: DNA
<213> ORGANISM: Homo sapiens

<400> SEQUENCE: 13
caaactaacc                                                          10
```

```
<210> SEQ ID NO 14
<211> LENGTH: 10
<212> TYPE: DNA
<213> ORGANISM: Homo sapiens

<400> SEQUENCE: 14
cgcagcgggt                                                            10

<210> SEQ ID NO 15
<211> LENGTH: 10
<212> TYPE: DNA
<213> ORGANISM: Homo sapiens

<400> SEQUENCE: 15
atgggatggc                                                            10

<210> SEQ ID NO 16
<211> LENGTH: 10
<212> TYPE: DNA
<213> ORGANISM: Homo sapiens

<400> SEQUENCE: 16
gttcacatta                                                            10

<210> SEQ ID NO 17
<211> LENGTH: 10
<212> TYPE: DNA
<213> ORGANISM: Homo sapiens

<400> SEQUENCE: 17
aagggagcac                                                            10

<210> SEQ ID NO 18
<211> LENGTH: 10
<212> TYPE: DNA
<213> ORGANISM: Homo sapiens

<400> SEQUENCE: 18
gaaataaagc                                                            10

<210> SEQ ID NO 19
<211> LENGTH: 10
<212> TYPE: DNA
<213> ORGANISM: Homo sapiens

<400> SEQUENCE: 19
ctcccccaag                                                            10

<210> SEQ ID NO 20
<211> LENGTH: 10
<212> TYPE: DNA
<213> ORGANISM: Homo sapiens

<400> SEQUENCE: 20
ctcccccaaa                                                            10

<210> SEQ ID NO 21
<211> LENGTH: 10
<212> TYPE: DNA
<213> ORGANISM: Homo sapiens

<400> SEQUENCE: 21
```
gttgtggtta 10

<210> SEQ ID NO 22
<211> LENGTH: 10
<212> TYPE: DNA
<213> ORGANISM: Homo sapiens

<400> SEQUENCE: 22
cctgggaagt 10

<210> SEQ ID NO 23
<211> LENGTH: 10
<212> TYPE: DNA
<213> ORGANISM: Homo sapiens

<400> SEQUENCE: 23
tgtcctggtt 10

<210> SEQ ID NO 24
<211> LENGTH: 10
<212> TYPE: DNA
<213> ORGANISM: Homo sapiens

<400> SEQUENCE: 24
ctaagacttc 10

<210> SEQ ID NO 25
<211> LENGTH: 10
<212> TYPE: DNA
<213> ORGANISM: Homo sapiens

<400> SEQUENCE: 25
ctcctcacct 10

<210> SEQ ID NO 26
<211> LENGTH: 10
<212> TYPE: DNA
<213> ORGANISM: Homo sapiens

<400> SEQUENCE: 26
tggggagagg 10

<210> SEQ ID NO 27
<211> LENGTH: 10
<212> TYPE: DNA
<213> ORGANISM: Homo sapiens

<400> SEQUENCE: 27
gacatcaagt 10

<210> SEQ ID NO 28
<211> LENGTH: 10
<212> TYPE: DNA
<213> ORGANISM: Homo sapiens

<400> SEQUENCE: 28
cttccttgcc 10

<210> SEQ ID NO 29
<211> LENGTH: 10
<212> TYPE: DNA
<213> ORGANISM: Homo sapiens

<400> SEQUENCE: 29

-continued

```
aaagcacaag                                                          10

<210> SEQ ID NO 30
<211> LENGTH: 10
<212> TYPE: DNA
<213> ORGANISM: Homo sapiens

<400> SEQUENCE: 30
gcccctgctg                                                          10

<210> SEQ ID NO 31
<211> LENGTH: 10
<212> TYPE: DNA
<213> ORGANISM: Homo sapiens

<400> SEQUENCE: 31
cccttgagga                                                          10

<210> SEQ ID NO 32
<211> LENGTH: 10
<212> TYPE: DNA
<213> ORGANISM: Homo sapiens

<400> SEQUENCE: 32
gatgtgcacg                                                          10

<210> SEQ ID NO 33
<211> LENGTH: 10
<212> TYPE: DNA
<213> ORGANISM: Homo sapiens

<400> SEQUENCE: 33
tttcctctca                                                          10

<210> SEQ ID NO 34
<211> LENGTH: 10
<212> TYPE: DNA
<213> ORGANISM: Homo sapiens

<400> SEQUENCE: 34
gatctcttgg                                                          10

<210> SEQ ID NO 35
<211> LENGTH: 10
<212> TYPE: DNA
<213> ORGANISM: Homo sapiens

<400> SEQUENCE: 35
cagctgtccc                                                          10

<210> SEQ ID NO 36
<211> LENGTH: 10
<212> TYPE: DNA
<213> ORGANISM: Homo sapiens

<400> SEQUENCE: 36
gcccccttcc                                                          10
```